(12) United States Patent
Davidson et al.

(10) Patent No.: US 6,286,376 B1
(45) Date of Patent: *Sep. 11, 2001

(54) SAMPLING OF A MIXTURE TO BE ANALYZED FOR PARTICLE SIZE/PARTICLE SIZE DISTRIBUTION

(75) Inventors: Gregory Paul Davidson, Ledbury; Stephen John Fielding, Upton-on-Severn; Robert James Henry Jennings, Gloucestershire, all of (GB)

(73) Assignee: Malvern Instruments Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,942

(22) Filed: Oct. 16, 1998

(30) Foreign Application Priority Data

Jan. 28, 1998 (GB) .................................................. 9801667

(51) Int. Cl.[7] .................................................. G01N 15/00
(52) U.S. Cl. ............................................................ 73/865.5
(58) Field of Search ................................ 73/61.65, 61.68, 73/61.69, 61.71, 61.56, 865.5, 863.01, 863.21, 864.81; 356/440–442

(56) References Cited

U.S. PATENT DOCUMENTS

| 4,015,628 | * | 4/1977 | Randolph . | |
| 4,619,136 | * | 10/1986 | Oritiz . | |
| 5,007,297 | * | 4/1991 | Sommer | 73/865.5 |
| 5,907,108 | * | 5/1999 | Garcia-Rubio et al. | 73/61.71 |

* cited by examiner

*Primary Examiner*—Robert Raevis
(74) *Attorney, Agent, or Firm*—Michael Best & Friedrich LLP

(57) ABSTRACT

A particle size distribution analysis sample dilution apparatus in which a sample consisting of a batch of a slurry of particles is deposited on an inclined plate of a progressive sample delivery system from which a continuous supply of water progressively washes off the sample and dilutes it. The initially diluted sample is further diluted with water continuously supplied in a funnel from which the further diluted sample passes under gravity along a conduit to a particle size distribution analyzer through which the diluted sample flows continuously. The conduit may include a mixing chamber to which water is continuously supplied to further dilute the sample prior to analysis.

21 Claims, 4 Drawing Sheets

SAMPLING OF A MIXTURE TO BE ANALYZED FOR PARTICLE SIZE/PARTICLE SIZE DISTRIBUTION

This invention relates to improvements in or relating to the sampling of a mixture to be analysed for particle size distribution, and to sampling apparatus therefor, which may include particle size distribution analysers and associated samplers.

BACKGROUND OF THE INVENTION

There are many times in industry when it is a requirement to measure the particle size characteristics of materials (often to check that a manufacturing process is operating correctly, or that materials that are to be input to a process are suitable). Processed slurries are an example of a kind of material that needs to be analysed in, for example, the mining and ore-extraction industry. In, for example, platinum refining it is common to have a slurry of ground and sieved ore and to want to ensure that the grinding and sieving operation is working properly. This will be taken as an example of a field where the invention has application, but should not be seen as being restrictive: the invention has applicability to many other fields.

A slurry is often far too concentrated to be passed through existing particle size distribution analysers (e.g. laser light scattering equipment). Slurries can be more than 50% solids whereas typical measurement conditions should be 1% or less solids. Up until now dilution of the slurry has been achieved by mixing a sample of slurry in a tank and then taking a sample volume of the diluted mixture. This process is slow: time needs to be allowed for the concentrated sample to be thoroughly mixed with the diluent (e.g. water). It is difficult to suspend large particles and when in suspension such particles have a tendency to differentially sediment. Furthermore, taking a small volume of a large volume of diluent with sample mixed in it has the possibility of large sampling errors: different sized particles mix in different ways, and simply taking out a bucket of mixture from a large tank of diluent plus sample can skew (or otherwise distort) measured particle size distribution significantly. Furthermore, after taking the sample from the diluted substance sample there is the problem of what to do with the remaining (vast majority) of the diluent plus sample. If the slurry/sample is toxic it may not be possible simply to pour it into a drain or river.

SUMMARY OF THE INVENTION

According to a first aspect of the invention we provide a particle size distribution analysis sample dilution apparatus comprising progressive sample delivery means adapted for delivering, in use, substantially the whole of the sample gradually to an analyser, coupling means adapted for coupling the apparatus to a particle size analyser for observing the size of particles in diluting liquid passed through the analyser, and diluting means adapted for continuously diluting the sample with the liquid prior to delivery of said liquid with its sample content.

By delivering substantially the whole of a sample to an analyser we void distortions of the measured particle size distribution which may be ntroduced in systems where a diluted mixture is itself sampled.

By progressively delivering the diluted sample to the analyser over time we enable a low concentration of particulates to be seen at the analyser.

The apparatus is adapted to run with liquid, usually water, flowing continuously through the progressive sample delivery means and/or the dilution means.

Preferably at least parts of the apparatus are self-cleaning in between testing samples. This is typically achieved by the continuous flow of water in the apparatus.

The progressive sample delivery means preferably delivers a sample to the dilution means spread out over a period that is in the range ½ minute to 10 minutes; or 1 minute to 5 minutes; and most preferably 2 minutes to 3 minutes. In one example it takes about 2½ minutes to deliver a full sample to the dilution means. The apparatus may be adapted to perform tests on successive samples at an interval of 10 minutes or less, and possibly at about 5 minutes intervals.

The dilution means may comprise a primary dilution unit adapted to receive the sample from the progressive sample delivery means and a secondary dilution unit adapted to receive primary diluted sample and also having a clean diluent input.

Preferably the secondary dilution unit comprises mixing means adapted to mix primary diluted samples with a much greater volume of clean diluent. The ratio of volume of primary diluted liquid to clean diluent mixed in the secondary dilution means may be in the range 1:50 to 1:2, and is preferably in the range 1:20 to 1:5, and is most preferably in the range 1:12 to 1:8. In one example, it is about 1 to 10.

The volume flow rate of diluted sample reaching the analyser may be at least 5 liters per minute, and possibly at least 10 litres per minute.

In one embodiment it is about 20 liters per minute, but it could be higher.

By having such a high volume flow rate we can dilute a sample by, say, 500 to 2000 times and still pass the whole sample through an analyser in a short time (e.g. about 5 minutes or under).

Preferably the primary dilution unit comprises a funnel.

Preferably the progressive sample delivery means comprises an inclined surface upon which a sample is deposited in use. The progressive sample delivery means may also comprise a diluent supply directed onto the inclined surface to progressively feed the sample, for example a sprayer adapted to spray diluent. Flow control means may be provided to control the supply of diluent to the progressive sample delivery means. The flow control means may be manually adjustable and/or under computer control).

The primary dilution unit and/or the progressive sample delivery means may comprise cleaning means adapted to clean it/them between the delivery of successive samples. An additional supply of diluent may be provided for these purposes and may be under computer control. Of course, the same supply of diluent may be used as opposed to the provision of an additional supply.

The primary dilution unit may have a liquid level sensor adapted to monitor the level of liquid within the primary dilution unit. The arrangement may be such that if the level of liquid falls below predetermined level additional diluent may be delivered to the primary dilution means. This may be used to prevent air from entering the apparatus.

There may be a diluent reservoir which supplies the primary dilution means and/or the secondary dilution means with clear diluent. We may prefer a head pressure/reservoir supply because it can give us a reserve should there be an interruption to the supply of diluent to the apparatus. A diluent supply line to the reservoir may have a sensor adapted to detect a failure or problem with a supply. The sensor could be a pressure sensor or a flow sensor or a temperature sensor (or any suitable sensor). An alarm may be activated should there be an interruption in the supply of diluent.

The apparatus may have no movable control valves which come into contact with sample or diluted sample. All of the controls may be in the supply lines for clean diluent. This helps to avoid problems associated with abrasive particles wearing components or blocking valves.

Similarly, there may be no pumps in contact with particles: all pumps may be provided clean diluent lines. No moving parts may be in contact with the sample.

Alternatively, or additionally particles may contact at least one pump which is provided to flush at least part of the apparatus of particles. However, such a pump may contact substantially only fine particles and so not be at risk of being damaged. Moreover, having only, this one pump in contact with particles reduces the number of pumps which are prone to wear, and we can arrange for the "flush pump" to be readily serviceable.

According to a second aspect of the invention we provide a particle size distribution analysis system incorporating apparatus in accordance with the first aspect of the invention, a particle size analyser, and a controller (e.g. a computer) arranged to control the apparatus.

The system may be adapted to react to the presence of particles above a predetermined size (e.g. to cause an alarm signal to be issued). Large particles may indicate a break in a sieve or screen.

The system may be adapted to react to a fall below a predetermined size in the size of particles passing through the analyser. We may arrange the system to consider that when the detected particle sizes are all below a threshold the true sample (or at least that portion of interest) has passed and that it is then looking at a low concentration contained in the fine tail of the distribution. This portion does not significantly contribute to the sample size distribution and so not measuring it does not significantly affect the measured distribution. The system may use this as a trigger to initiate a cleaning operation to clean itself/reject/extract the remaining tail of the diluted "sample", ready for the next sample. The system may be so designed that the larger size particles reach the analyser first, leaving progressively more dilute finer portions to flow through later. It will be appreciated that the system is designed to segregate particles according to size, and depending upon the actual conditions either the larger or smaller sized material could reach the analyser first.

According to another aspect of the invention we provide a method of diluting a particulate sample prior to analysing it, said method comprising delivering substantially the whole of a sample for analysis progressively spread out over time to enable the analysis to see substantially all particles of said sample, said sample being diluted by a liquid and delivered progressively for said analysis, and supplying said liquid continuously for continuously diluting the sample prior to performance of said analysis.

This avoids the particles appearing as an opaque slug at an analyser and thus saturating the analyser.

Preferably the method comprises continuously running diluent through progressive sample delivery means. Preferably diluent is run continuously through dilution means.

The method may comprise a continuous process of diluting the sample bit by bit in a primary dilution step and then diluting the primary diluted material again in a secondary dilution step, the secondary dilution of some of a sample occurring whilst the primary dilution of another portion of said sample is occurring, and preferably the primary and secondary dilution of different portions of the sample occurring prior to other portions of the sample being primarily diluted.

Typically, the finer particles may be released from/are led off the progressive sample delivery means before the coarser particles. Some coarser particles may also be delivered right at the early stages of a test.

The method may comprise providing a reservoir of diluent to provide a buffer against failure of diluent supply.

The method may comprise controlling the degree of dilution of the sample so as to achieve a predetermined concentration of particles of a predetermined size (or size range) at the analyser.

The sample may have a large volume, preferably at least 10 ml, most preferably at least 40 ml, or 50 ml, or 60 ml or 70 ml or more. The combination of large sample and high flow rates enables us to do a test run on a sample in around 5 minutes or so (in one embodiment).

The system is preferably capable of analysing particles in the range 1 $\mu$m –1000 $\mu$m, and may be fully automated, requiring no human intervention.

The system may run a background measurement, which may be run in the clean diluent flow. This may be used to correct distortion of the analyser and can be used to take account of a small amount of contamination on the analyser's optical surfaces.

We may be able to clean the primary dilution means and progressive sample delivery means in about 1 minute.

According to a further aspect of the invention we provide a method of cleaning a progressive sample delivery means comprising:

i. suspending adding further sample;
ii. continuing to add diluent;
iii. allowing the diluent and sample to pass through the delivery means.

This has the advantage that sample can be washed through the delivery means before further sample is added.

The method may further comprise pumping from the delivery means diluent and sample which has failed to pass through the delivery means. An advantage of such pumping is that the delivery means can be made ready to receive the next sample earlier.

The pumping may occur after a pre-determined time has elapsed from the beginning of the sample. Alternatively the pumping may occur once particles above a pre-determined size are no longer present in the sample. (This may be determined by a particle analyser connected to the delivery means).

According to a further aspect of the invention there is provided a progressive sample delivery means adapted to gradually deliver, in use, substantially the whole of a sample to coupling means which is adapted to couple the delivery means to an outside apparatus, and dilution means adapted, to dilute the sample with a liquid prior to its delivery to said coupling means, the delivery means being adapted, in use, for utilizing aforesaid liquid.

The progressive sample delivery means may have any of the features disclosed in relation to the first aspect of the invention.

The outside apparatus may be a particle size distribution analyser.

BRIEF DESCRIPTION OF THE DRAWINGS

The invention will now be further described by way of example, with reference to the accompanying drawings of which

DESCRIPTION OF PREFERRED EMBODIMENTS

Figure 1:
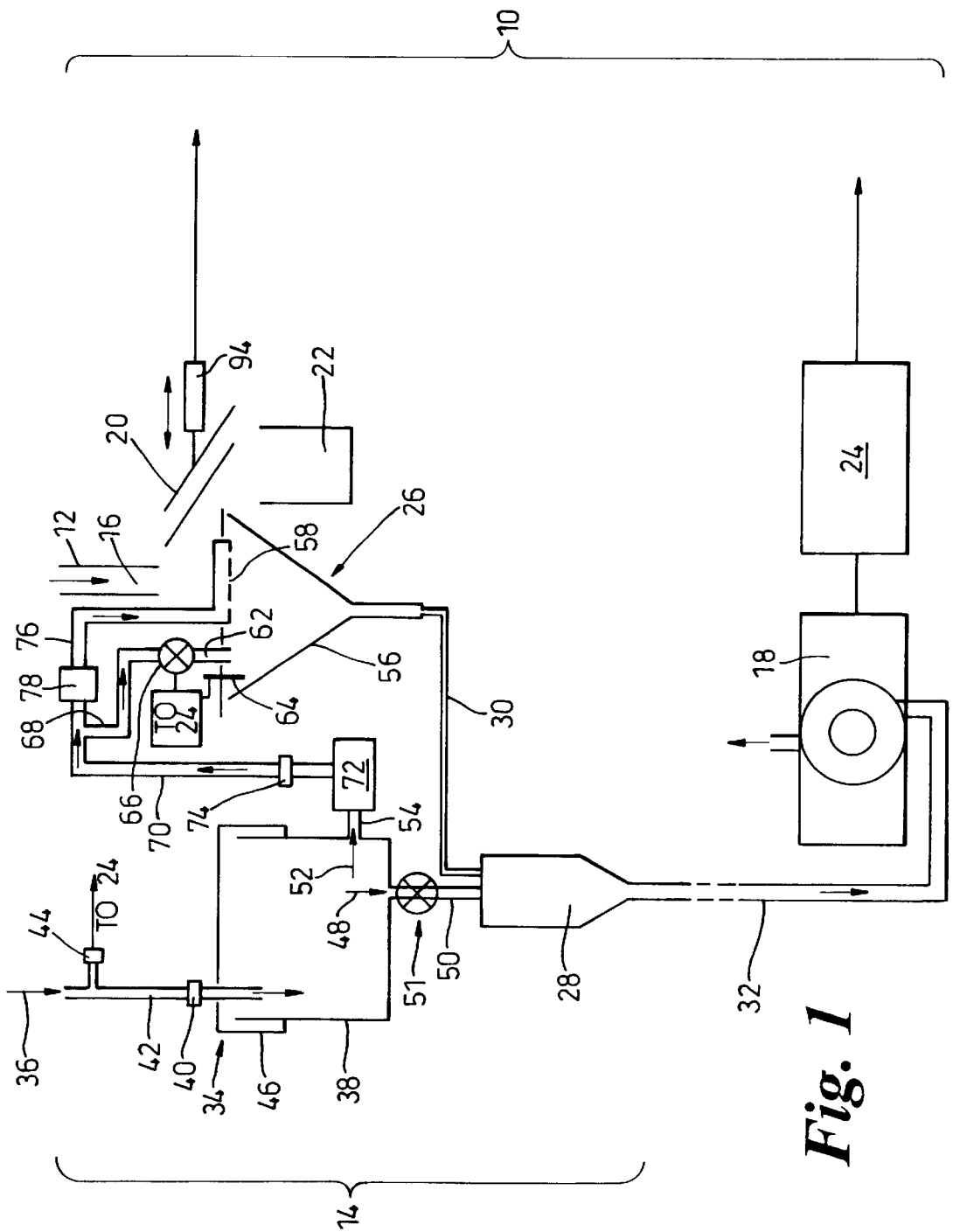
FIG. 1 shows schematically a slurry sampling and dilution system, and associated particle size distribution analyser.

A sampling system 10 adapted to sample a slurry and analyse the particle size distribution of the slurry is shown in FIG. 1 and comprises means 12 for sampling the slurry output of a process (e.g. in this case sampling processed platinum ore) which in this example is a Vezin sampler of known kind, sample dilution means 14 to which the Vezin sample (reference 16) is fed, and sample particle size distribution analysis means 18 which receives the diluted sample from the sample dilution means 14. Also present is a sample divert mechanism 20 adapted to divert some sample from the Vezin sampler/cutter 12 to a compounded sample vessel 22, the compounded sample comprising a primary reference sample for off-line testing in a laboratory. (Assays can be performed on the diverted compounded sample, and other off-line particle size distribution tests can be carried out to check the accuracy of the on-line/on-site analyser 18). The analyser 18, and indeed the rest of the sampling system 10, is controlled by a computer controller 24, such as a P.C.

The sample dilution means 14 comprises a primary dilution unit 26 which feeds its output to a secondary dilution unit 28 via pipework 30.

The secondary dilution unit 28 also acts as mixing means and provides a much diluted output to analyser 18 via pipework 32. There is also a clean water supply unit 34.

The system is arranged so that the water/diluted particles arrive at the analyser at a pressure of about 1 bar.

The clean water supply unit has an input 36 of clean water which feeds into a large tank 38 (volume typically 100 liters). The tank itself may be fed water from a larger reservoir tank (not shown) of 2000 liters or more, and also having a sensor on the water input pipe serving to detect failure of the supply and feeding signals to the computer 24.

A flow control regulator 40 is provided in supply pipe 42 leading to the tank 38. The flow control regulator may be a mechanical fitting or it may be under the control of the computer 24. A pressure sensor 44 is provided to monitor the pressure in supply pipe 42 and provides water supply failure warning signals to the computer 24. A cover 46 is provided on the tank 38 to avoid contamination of the water in the tank.

The tank 38 has a first water outlet 48 which provides water to the secondary dilution unit/mixer 28 via pipework 50, and a second water outlet 52 which provides water to the primary sample dilution unit 26 via pipe 54. A control valve 51 is provided within the pipework 50 to ensure the flow rate from the tank 38 to the secondary dilution unit 28 is as desired.

The skilled person will realise that should sufficient dilution be realisable within the funnel 56 then the secondary unit 28 may not be necessary and the sample plus diluent would then flow from the funnel 56 straight to the sample analyser 18. Conversely, should not enough dilution be realised even after the secondary dilution unit, tertiary or even quaternary dilution units may be provided. It will be further realised that the output of one dilution unit would then flow into the next.

Figure 2:
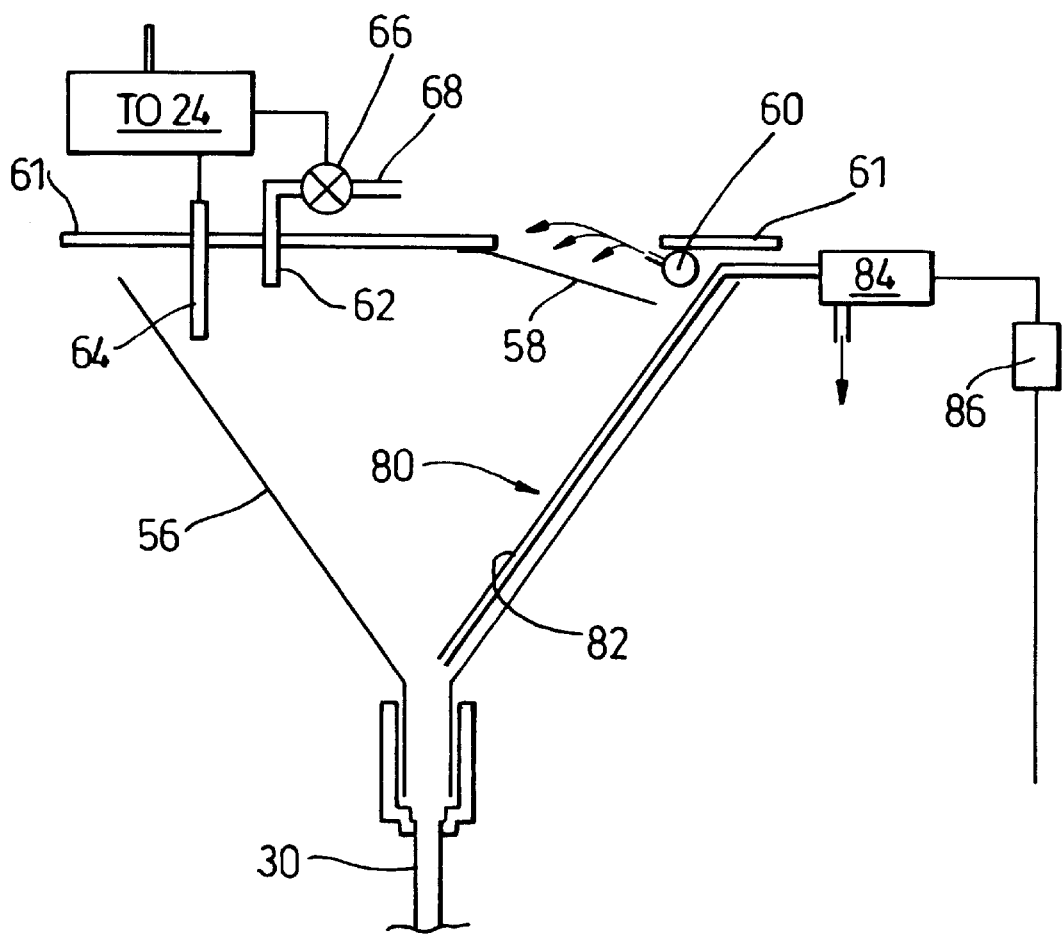
FIG. 2 shows schematic detail of a primary dilution unit of the apparatus of FIG. 1.

The primary sample dilution unit 26 is best shown in FIG. 2 and comprises a chamber, in this case a funnel 56 which feeds pipework 30, a progressive feed sample delivery means, in this case an inclined plate 58, a clean water delivery to the progressive feed sample delivery means, in this case a sprayer 60 which, in use, directs a spray of water onto at least the upper portion of the inclined plate 58, a clean water supply to the funnel via pipe 62, and a water level sensor 64 which feeds signals to the computer 24 to maintain an adequate water level within the funnel 56. If the water level within the funnel 56 is allowed to fall too low air can enter the system which can affect the results obtained. Preferably the sprayer 60 sprays water over the whole of the plate 58.

The volume of the funnel 56, in this example, is approximately 3 liters. The upper limit on this value is set by the need to pass all of the funnel contents at a flow rate of 2½ min (as discussed hereinafter) in a period of approximately 3 minutes. Therefore less than 10 liters is required. The lower limit is set by the need to have a minimum depth to prevent air entering the pipework 30 but to maintain a suitably steep profile to the sides (this is expected to set a minimum volume of approximately ½ liter).

The clean water is supplied to the pipe 62 via valve 66 and pipework 68 which communicates with pipework 70 (see FIG. 1) which is in turn provided with clean water from pipe 54 leading from tank 38. A pump 72 (see FIG. 1) is provided to pump water from tank 38 to pipework 70. (However, water could also be gravity fed from the tank 38 to the funnel 56. It will be realised that a suitable control valve would then be needed). A pressure regulator 74 is provided in pipework 70 and may be a mechanical assembly, or may be under the control of the computer 24. A sensor (not shown) may be provided to detect the pressure in the portion of the pipe 70 between the pump 72 and the pressure regulator 74 (or at some other location in the water supply pipework of the primary dilution unit).

Water is supplied to the sprayer 60 via pipework 76 which communicates with pipe 70 via a flow controller 78, in this case a needle valve, which may be under the control of the computer 24. The flow controller 78 is provided downstream of the junction of pipe 68 with pipe 70. A cover 61 extends over the funnel 56 and prevents contaminants from falling into the funnel.

The funnel 56 also has associated with it an extractor 80 which is adapted to extract liquid in the funnel to avoid the need for the contents of the funnel necessary to pass through the secondary dilution/mixer unit 28; and the analyser 18. This can be useful if the sample is to be changed, or no further analysis of a sample in the system needs to be performed. Extracting the contents of the funnel can save time. The extractor 80 comprises an extraction tube 82 extending along the wall of the funnel to the outlet of the funnel (where in use liquid enters the extraction tube 82), a pump 84 which pumps out liquid in the tube 82, and a pump relay 86 which controls the pump 84. The pump relay is under control of the computer 24. The valve 66 of the clean water supply to the funnel is also under control of the computer 24 and fresh water may be introduced into the funnel to assist in cleaning it ready for the next sample.

It will be realised that if the extractor 80 and pump 84 are used to empty the funnel 56 before the tail of the distribution has been allowed to pass through the system small particles may pass through the pump 84. However, these are small enough so as not to cause damage to the pump. Pump 84 is the only pump through which particles can pass.

Critical control elements (those that affect the measured flow that reaches the analyser) operate on clean water. The non-critical emptying of the funnel 56 does operate on dirty water, but the liquid does not reach the analyser.

Figure 3:
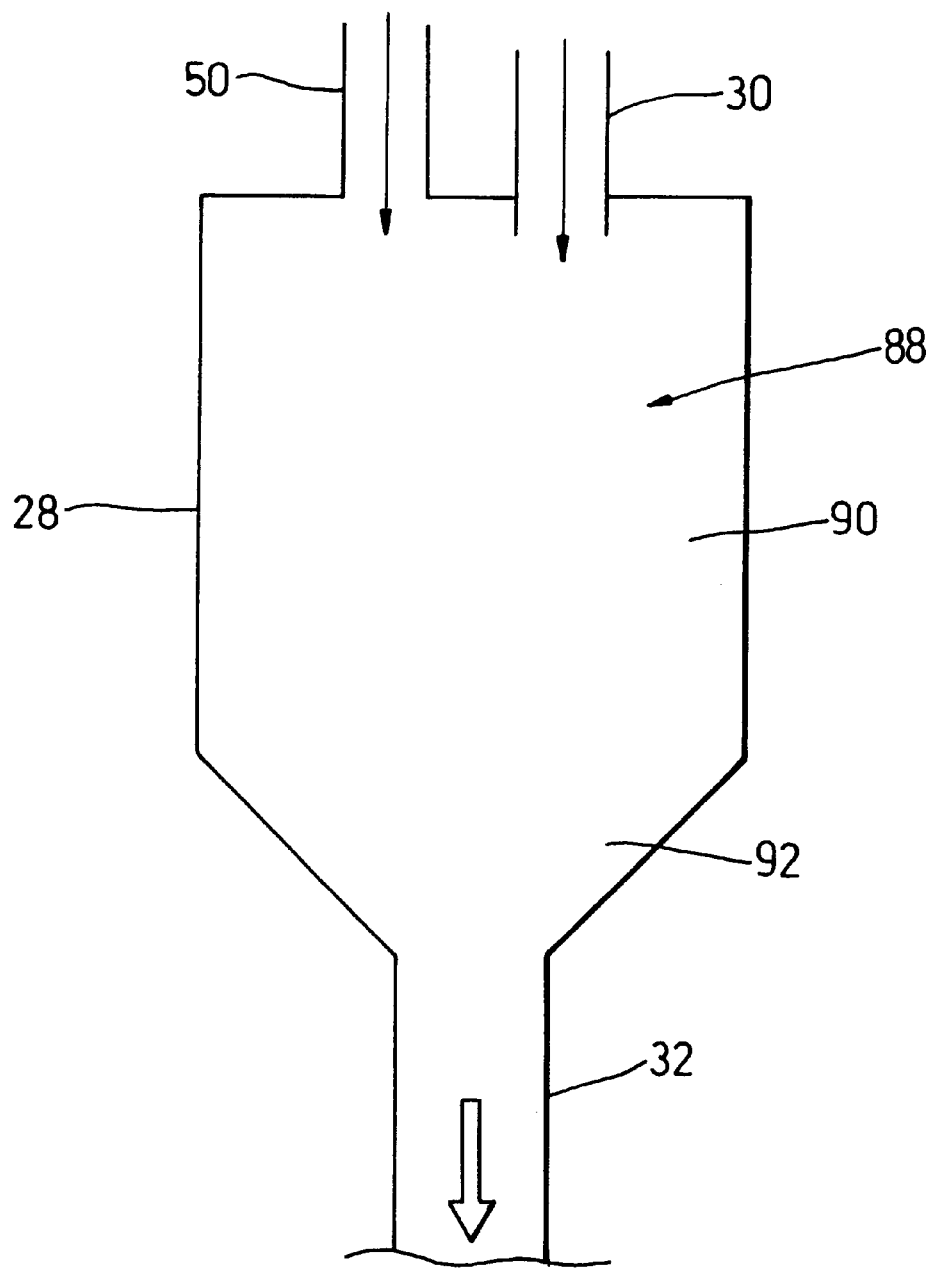
FIG. 3 shows schematic detail of a secondary dilution unit of the apparatus of FIG. 1.
Figure 4:
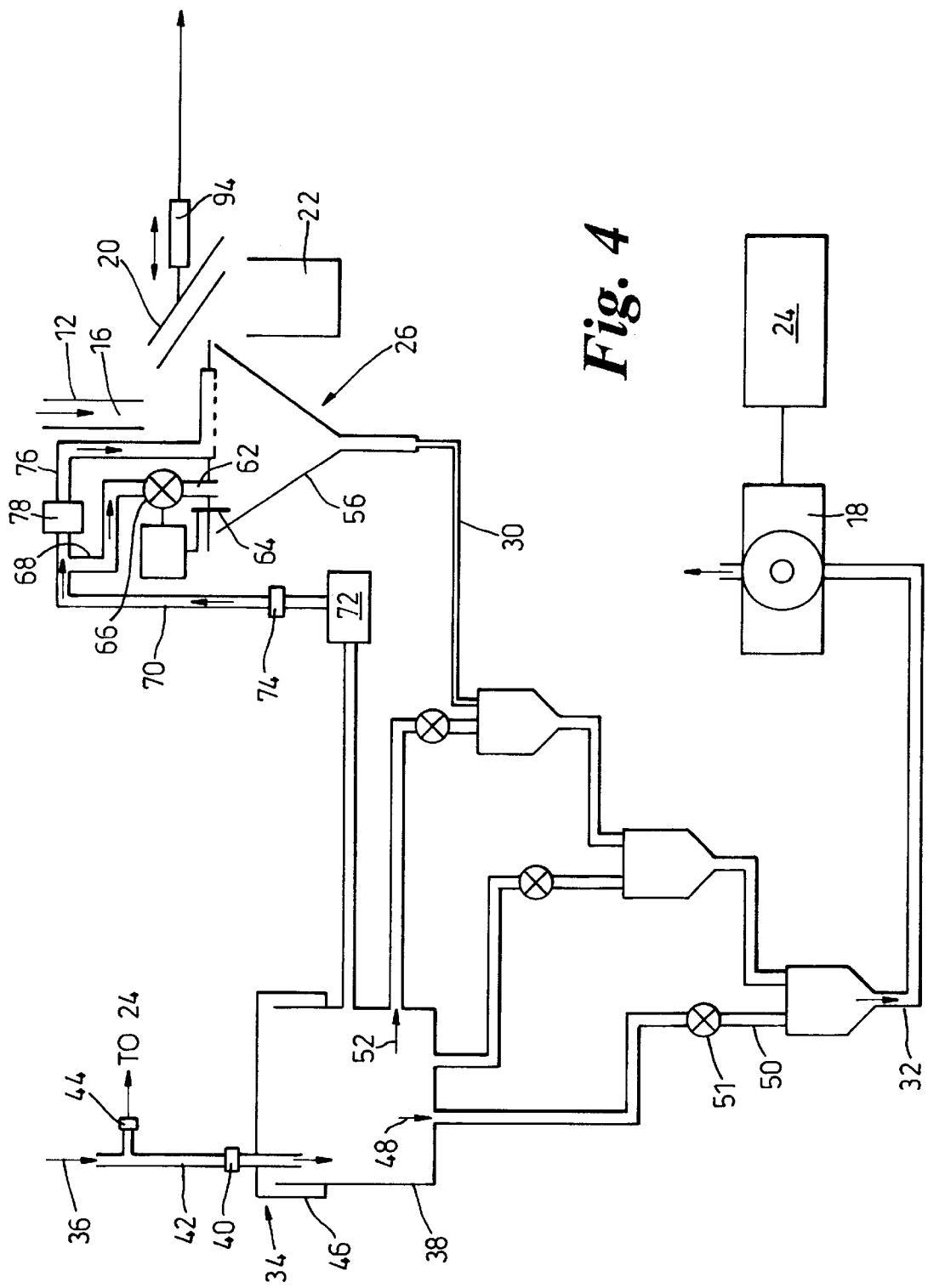
FIG. 4 shows schematically a slurry sampling and dilution system, and associated particle size distribution analyzer with dilution units in addition to those of FIG. 1.

Further schematic details of the secondary dilution unit are shown in FIG. 3. The clean water inlet of pipe 50 is at the top of a mixing chamber 88 provided in the unit 28. The mixing chamber 88 is a generally cylindrical chamber 90 having a conical lower region 92. The pipe 30 coming from the primary dilution unit is shown as protruding a little way into the mixing chamber 88. It may do this, or it may terminate at the wall of the chamber in a similar manner to pipe 50, or may be extended into the secondary dilution unit 28 as a spiral. It is advantageous to cause turbulence within the secondary dilution unit 28 to mix the two flows. The two liquid inlet pipes 30 and 50 are arranged so as to achieve turbulent mixing of their liquids, and hence further dilution of the primary diluted sample.

The sample divert mechanism 20 discussed earlier, and shown in FIG. 1, is operated by a pneumatic/or hydraulic/or mechanical control system 94 which is controlled by the computer 24.

The operation of the sampling system 10 will now be discussed.

A slurry sample is taken by the Vezin cutter and deposited by the sample divert mechanism 20 on the inclined plate 58. The funnel 56 is full of clean water at this point and water is entering the funnel via pipe 62 and leaving the funnel via pipe 30. About 2.5 liters per minute flow down the pipe 30 to mixer 28.

Tank 38 is fed clean water from the water supply 36 and about 18 litres per minutes of clean water flows down pipe 50. The two flows from pipes 30 and 50 are mixed in mixer 28 and fed down pipe 32 at about 20 liters per minute, and the whole of this 20 liter per minute flow passes through the analyser 18. By suitable choice of the diameter of pipes 30 and 50 both the flows may be adjusted to suit local conditions.

The sprayer 60 is operating continuously. When a slurry sample is deposited on sloping plate 58 (progressive feed delivery means) the undiluted slurry sample may have the consistency of thick mud, and has within it a range of particle sizes. A spray of clean water from the sprayer 60 washes, gradually over a period of time (1 to 3 minutes) the sample of the plate 58 into the funnel 56. The angle of the slope of the plate and the volume and pressure of spray control the rate at which the sample is washed off the plate. Different sized particles may have a tendency to come off the plate at different times, but because of the slope of the plate, some heavier particles enter the funnel earlier than they would if the plate were horizontal. This spreads out the larger/heavier particles in the stream of liquid delivered to the analyser, which avoids a "plug" of large particles reaching it all at once, which would be difficult to analyse reliably.

There is some variability in the rate at which particles of similar sizes are washed from the plate depending amongst other things on the sizes of the particles, whether the particles are covered by the spray or uncovered, and on their position on the plate 58. Typically smaller sized particles are washed from the plate 58 before larger particles. However, if large (or relatively large) particles occur near the edge of the plate 58 then it is likely that these larger particles are washed into the funnel 56 before smaller particles further from the edge of plate 58. There is thus a mixture of different sized particles entering the funnel 56 at any one time.

The water level sensor 64 and the computer 24 ensure that the water level in the funnel is maintained above a predetermined height. This avoids air/bubbles entering the pipe 30, which can make analysis of the particle size distribution difficult or impossible. Valve 66 and/or flow control 78 are controlled by the computer to ensure adequate water in the funnel.

When a portion of a sample is washed into the funnel 56 it is primary diluted and is passed to the secondary dilution unit/mixer 28 where it is mixed with a much larger volume of water and fed to the analyser 18. The liquid that leaves the analyser can be fed to waste, or recycled to a reclamation process. It will be realised by the skilled person that liquids other than water could be used as the diluent in which case the liquid would usually be recycled or reclaimed. The liquid may for example be alcohol.

Over a 1 to 3 minute period all of the sample deposited on the plate 58 is washed into the funnel 56. As will be appreciated the delivery of the sample to the analyser is spread out over time, but all of the sample is passed through the analyser and analysed. Thus signals representative of substantially all particles in a sample are collected by the analyser. This avoids problems associated with sampling a sample. Sampling a sample can easily introduce sampling errors and biases to distort the detected particle size distribution; passing the whole sample through the analyser avoids this. Spreading the effective delivery of the sample, especially larger particles, out over time also facilitates analysis.

The present embodiment passes a sample through the system in about 3 minutes. If a further minute or so is allowed for the system to self-clean (if the sprayer operates continuously, spraying water over the whole of the plate, the plate will be cleaned, and the other fluid flows are continuous) then we may be ready to operate sampling at, say, 5 minute intervals. This is very fast compared with known sampling systems where a cycle of 30 minutes may be typical.

Our system has continuous flow, and has very little, or no, need for manual intervention. The system can run for days conducting checks every 5 minutes on the particle size distribution of samples, and hence monitoring the correct performance of the processes.

It will be noted that the system has no moving parts/ control valves (with the exception of pump 84 noted above which is a non-critical pump and only operates on very fine dilute particles) which operate on the slurry, or slurry-containing diluent (and no pumps or valves, which operate on the main particle-containing liquid flowing to the analyser). The only control valves are in the clean water supply. This has the advantage that it avoids abrasion/wear on moving parts/control surfaces that particulate material can cause. Clogging or wear of valves could be a significant problem if valves were used to control flowing slurry, even diluted slurry.

As some commercial environments, e.g. mining operationslore processing operations are far from civilisation, it can be difficult to guarantee a continuous clean water supply —there can be interruptions.

This is one reason why we prefer to have a large reservoir tank, as our source of pressurised water for tank 38. Pressure sensor 44 can inform the computer if the water supply falls low, or is interrupted. If the tank has 2000 liters and is running at about 20 liters per minute we would have perhaps 100 minutes warning of an interruption, and we could work through short interruptions of an hour or so. Of course a bigger reservoir would give us a bigger buffer, and more capacity to work through water supply interruptions. We could, of course, have a sensor on the in-flow line of the large reservoir tank (not shown) to detect an interruption in "mains" water supply.

In the present embodiment we prefer to use a gravity feed tank as a source of pressurised clean water with a head of about 8 meters above the analyser 18.

The flow control 78 has a needle valve which is manually set initially to allow for local conditions. It is set so that most of the flow into the funnel 56 comes via the sprayer (or even all of the flow to the funnel) during the sample analysing phase of operation.

The computer receives the output signal from the analyser 18 and can detect the start of signals from a sample (when particles begin to be detected), and can detect the end of signals from a sample (when particles stop being detected). When it stops detecting particles it operates valve 66 and pump 84 to introduce fresh water into the funnel at the top, and pump most of it out again at the bottom, to clean the funnel ready for the next sample (but at all times allowing 2.5 liters/minute to flow through pipe 30). Pipe 30, mixer 28 and pipe 32 (and the analyser itself) are self-cleaning in between samples tests since clean water will continuously flow through them. Pipe 50 has an internal diameter of about 15 mm. Pipe 30 has an internal diameter of about 8 mm. The diameters of the pipes may be adapted to attain first order optimised flows for the specific material to be analysed.

It will be appreciated that the smallest particles will take the longest time to settle through the mixer 28 and reach the analyser 18. Therefore, the smallest particles present may take too long to reach the analyser 18 to enable the cycle time to be kept within the desired range. Therefore, once the analyser 18 detects only particles below a predetermined size or the time delay between detecting particles is too long then the cleaning operation may be started.

The very fine residue tail may need to be pumped away (it may not wash through in a time scale consistent with continuous sampling. The small particles however, contribute to an insignificant part of the particle size distribution).

The system can also detect problems in the processing of the slurry sample and alert other systems, or activate an alarm. For example, if particles above a predetermined size are detected this may indicate a hole in a sieve or screen.

The system may have provision to provide an input signal indicative that a sample is about to be introduced to the funnel, and have provision to take account of this or to generate a signal which indicates delivery of the primary sample.

The analyser may provide optimum analysis of a particular particle size range of interest at an appropriate dilution of the sample. The computer may control the flow controller 78 (if it is electronically controlled) and/or the valve 66 and/or valve 40 to vary the concentration of the sample at the point of analysis so as to optimise the analysis. This feedback may operate continuously, or it may be selectable by a user.

The computer may control the pressure of the spray coming from sprayer 60 (by controlling the pump 72 or a control valve (not shown), and/or its direction (the sprayer may be movable, e.g. pointable or bodily movable, under computer control), the angle of tilt of plate 58, the speed of cycle between samples and dilution. All of the controls may be under computer control, but may additionally or alternatively be manually adjustable.

As an alternative to tilting the plate 58 the plate could be spun, perhaps, at varying speeds, to alter the rate at which particles are washed from the plate.

It will be appreciated that the inclined plate 58 spreads out the delivery of the sample over time. This delayed or progressive sample delivery delivers the fine particles first, and then the heavier particles (but still spreads out the heavier particles to avoid a plug) and can be achieved by other means, such as by using a spinning plate/disc, or by putting the sample in a trough and tipping the trough progressively, or by a panning operation.

Instead of using a gravity fed clean water system we may use a pump. To achieve mixing in the mixer/secondary dilution unit we may use a venturi effect to drag the primary diluted liquid on, but we prefer to use head pressure and turbulence to achieve better mixing.

A typical sample may be about 50 ml slurry having about 40 ml of solids. This gets mixed with water at 20 liters/minute over 3 minutes, which gives a dilution of about 1200 times. This sample size, 50 ml, is big in comparison with other systems, and this enables us to more accurately sample small concentrations of large particles.

The ability to have feedback to alter the dilution ratio can be provided in either arm of the water delivery system.

It will be appreciated that the system is fully automated, is robust and has low maintenance, and that a high volume throughput allows us to dilute the whole of the sample, and test the whole of the sample. The sample is passed through once, without re-circulating it. This introduces less bias than other systems, as does spreading the sample out over time. The system may detect particles from about ½ $\mu$m to 800 $\mu$m or more, possibly even to 1000 $\mu$m (or more).

The system stops itself if it knows there will not be enough water for a test cycle. This prevents damage or blockage, and avoids time and expense in re-starting since it still keeps out air. The analyser 18 operates in a continuous loop, performing background and sample measurements and calculations, and reporting. It as a local memory to keep most data, but can also export reports periodically via telecommunications links to the plant process controller as required.

The system can accommodate stoppages for routine maintenance: the computer leaves the system full of water so as to prevent air bubbles forming. Air bubbles within the system can effect the results output by the analyser.

We claim:

1. A particle size distribution analysis sample dilution apparatus, the apparatus comprising:

a plurality of dilution units, at least one dilution unit being in fluid communication with another dilution unit;

at least one water supply unit providing a flow of diluent into the dilution units to progressively dilute a particle sample; and a particle size analyser coupled to at least one of the dilution units to receive the whole of the particle sample in the analyser to observe the size of particles in the sample.

2. The particle size distribution sample dilution apparatus according to claim 1, wherein at least one water supply unit provides a continuous flow of diluent to the particle size analyser during operation.

3. The particle size distribution-sample dilution apparatus according to claim 1 or 2, wherein one of the dilution units comprises an inclined surface for deposit thereon of the particle sample, and at least one of the water supply units provides a flow of diluent onto the inclined surface.

4. The particle size distribution sample dilution apparatus according to claim 1, wherein the dilution units include a primary dilution unit adapted to receive the sample for initial dilution and a secondary dilution unit adapted to receive the diluted sample from the primary dilution unit for further dilution of the sample.

5. The particle size distribution sample dilution apparatus according to claim 4, wherein one water supply unit has a water inlet pipe extending therefrom to provide a flow of diluent to the primary dilution unit and another water inlet pipe extending therefrom to provide a flow of diluent to the secondary dilution unit.

6. The particle size distribution sample dilution apparatus according to claim 4, wherein the particle sample is diluted by a factor of at least 2 in the secondary dilution unit compared to the dilution of the sample in the primary dilution unit.

7. The particle size distribution sample dilution apparatus according to claim 4, wherein one or more dilution units are further provided to receive the diluted sample from the secondary dilution unit and to further dilute the sample.

8. The particle size distribution sample dilution apparatus according to claim 1, wherein the water supply unit provides diluent to the analyser at a rate of at least five liters per minute.

9. The particle size distribution sample dilution apparatus according to claim 1, wherein the sample is delivered to the analyser substantially within a pre-determined time.

10. The particle size distribution sample dilution apparatus according to claim 1, wherein the apparatus is arranged to perform tests on successive samples at pre-determined intervals.

11. The particle size distribution sample dilution apparatus according to claim 1, wherein at least one water supply unit provides clean diluent between successive tests at a rate sufficient to clean the apparatus.

12. The particle size distribution sample dilution apparatus according to claim 1, wherein a single pipework provides the only channel through which diluent can egress from the dilution units connected to the analyser.

13. The particle size distribution sample dilution apparatus according to claim 1, wherein at least one dilution unit and at least one water supply unit gradually dilutes the sample.

14. A method of diluting a particle sample prior to analysis of the size of particles in the sample comprising:

providing a particle sample for analysis;

providing a supply of diluent;

progressively diluting the sample over time using a primary dilution for initially diluting the sample and a secondary dilution for further diluting the diluted sample subsequent to the primary dilution wherein the secondary dilution of one portion of the sample occurs concurrently with the primary dilution of another portion of the sample; and progressively delivering the whole of the diluted sample to a particle size analyser for evaluation of the size of particles in the sample.

15. The method according to claim 14, wherein the diluent continuously dilutes the sample and continuously flows through the analyser.

16. The method according to claim 14, wherein a reservoir of diluent provides a flow of diluent in case of water supply failure.

17. The method according to claim 14, wherein the degree of dilution of the sample is controlled so as to achieve a predetermined concentration of particles of a predetermined size.

18. The method according to claim 14, wherein the volume of diluent diluting the sample is in the range of about 40 mL to about 70 mL.

19. The method according to claims, wherein the particle size of sample tested is substantially in the range of 1 $\mu$m to 1000 $\mu$m diameter.

20. The method according to claim 14, wherein diluting the sample over time provides for a gradual dilution of the sample.

21. A particle size distribution analysis sample dilution apparatus, the apparatus comprising:

a plurality of dilution units, at least one dilution unit being in fluid communication with another dilution unit;

at least one water supply unit providing a flow of diluent into the dilution units that progressively dilutes a particle sample; and a particle size analyser coupled to at least one of the dilution units to receive a continuous flow of diluent and to receive substantially the whole of the particle sample to observe the size of particles in the sample.

* * * * *